United States Patent
Daugherty et al.

(10) Patent No.: US 7,193,055 B2
(45) Date of Patent: Mar. 20, 2007

(54) COMPACTION ASSAY FOR ASSESSMENT OF RESPIRATORY DISEASE THERAPY

(75) Inventors: Ann L. Daugherty, Palo Alto, CA (US); Randy J. Mrsny, Redwood City, CA (US); Thomas W. Patapoff, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 108 days.

(21) Appl. No.: 11/033,358

(22) Filed: Jan. 10, 2005

(65) Prior Publication Data

US 2005/0164334 A1 Jul. 28, 2005

Related U.S. Application Data

(63) Continuation of application No. 10/162,951, filed on Jun. 4, 2002, now abandoned, which is a continuation of application No. 09/771,078, filed on Jan. 25, 2001, now abandoned, which is a continuation of application No. 08/840,441, filed on Apr. 1, 1997, now abandoned, which is a continuation of application No. 08/539,468, filed on Oct. 5, 1995, now abandoned, which is a continuation of application No. 08/355,418, filed on Dec. 13, 1994, now abandoned, which is a continuation of application No. 08/132,681, filed on Oct. 6, 1993, now abandoned, which is a continuation of application No. 07/971,019, filed on Nov. 2, 1992, now abandoned.

(51) Int. Cl.
C07K 14/00 (2006.01)
(52) U.S. Cl. ..................... 530/350; 530/399
(58) Field of Classification Search ................ 530/350, 530/399
See application file for complete search history.

(56) References Cited

U.S. PATENT DOCUMENTS

| 3,914,985 A | 10/1975 | von Behrens |
| 4,072,045 A | 2/1978 | Kopito |
| 5,364,763 A | 11/1994 | Kacian |

FOREIGN PATENT DOCUMENTS

| EP | 0285439 B1 | 9/1994 |
| SU | 460868 | 9/1975 |

OTHER PUBLICATIONS

Aiken et al., "Recombinant Human DNase Inhalation in Normal Subjects and Patients with Cystic Fibrosis" *Journal of the American Medical Assn.* 267(14):1947-1951 (Apr. 1992).
Boat et al., "Cystic Fibrosis" *The Metabolic Basis of Inherited Disease*, Scriver et al., McGraw Hill, Chapter 108, pp. 2646-2680 (1989).
Clifton et al., "Pancreatic Deoxyribonuclease (Dornase) Aerosol in Treatment of Bronchopulmonary Complications and Tracheitis Sicca" *Cancer* 14:414-420 (Mar.-Apr. 1961).
"Database WPI, Week 7541, Derwent Publications Ltd., London, GB; AN 75-L1806W and SU A 460 868 (Work Hygiene Profes)" (Abstract only) (1975).
Dulfano et al., "Sputum Viscoelasticity in Chronic Bronchitis" *Am. Rev. Respir. Dis.* 104:88-98 (1971).
George et al., "Pseudomonas Infections in Cystic Fibrosis" *Archives of Dis. Childhood* 62:438-439 (1987).
Hubbard et al., "A Preliminary Study of Aerosolized Recombinant Human Deoxyribonuclease I in the Treatment of Cystic Fibrosis" *New England J. of Medicine* 26(12):812-815 (Mar. 1992).
Karem et al., "The Relation Between Genotype and Phenotype in Cystic Fibrosis—Analysis of the Most Common Mutation" *New England J. of Medicine* 323(22):1517-1522 (Nov. 1990).
King, M., "The Role of Mucus Viscoelasticity in Cough Clearance" *Biorheology* 24:589-597 (1987).
Lethem, M. et al., "The origin of DNA associated with mucus glycoproteins in cystic fibrosis sputum" *Eur. Respir. J.* 3:19-23 (1990).
Lopez-Vidriero et al., "Respiratory tract fluid—chemical and physical properties of airway mucus" *Eur. J. Respir. Dis.* 61(Suppl. 110):21-26 (1980).
Matthews et al., "Studies on Pulmonary Secretions" *Am. Rev. Respir. Dis.* 88:199-204 (1963).
Montalembert et al., "Antimicrobial Treatment in Cystic Fibrosis" *Ann. Pediatric.* 38(8):523-528 (1991).
Mulherin et al., "Aminoglycoside Induced Ototoxicity in Patients with Cystic Fibrosis" *Irish Journal of Medical Science* 160(6):173-175 (Jun. 1991).
Mulherin et al., "Cystic Fibrosis in Adolescents and Adults" *Dig. Dis.* 10(1):29-37 (1992).
Nelson et al., "Decomposition of Expoploysaccharide Slime by a Bacteriophage Enzyme" *Water Res.* 22:1185-1188 (1988).
Picot et al., "Pus, deoxyribonucleic acid, and sputum viscosity" *Thorax* 33:235-242 (1978).
Raskin, Philip, "Bronchospasm After Inhalation of Pancreatic Dornase" *Am. Rev. of Respiratory Disease* 98:697-698 (1968).
Reid, L., "Rheology-Relation to the Composition of Sputum" *Scandinavian J. of Respiratory Diseases*, Munkgaard International Publishers vol. 103:27-35 (1974).
Rosenbluth et al., "Influence of Mist Tent Therapy on Sputum Viscosity and Water Content in Cystic Fibrosis" *Arch. of Dis. Childhood* 49:606-610 (1974).

(Continued)

*Primary Examiner*—Karen Cochrane Carlson
(74) *Attorney, Agent, or Firm*—David W. Evans

(57) ABSTRACT

A compaction assay measuring the viscoelasticity of sputum samples of patients subject to respiratory disease is provided. This assay is useful in determining the therapeutic efficacy of DNase, antibiotic and other respiratory disease treatments in improving lung function.

22 Claims, 8 Drawing Sheets

OTHER PUBLICATIONS

Shak et al., "Recombinant Human DNase I Reduces the Viscosity of Cystic Fibrosis Sputum" *Proc. Natl. Acad. Sci. USA* 87(23):9188-9192 (Dec. 1990).

Thornton et al., "Mucus glycoproteins from cystic fibrotic sputum" *Biochemical Journal* 276:667-675 (1991).

Vasconcellos, C. et al., "Reduction in viscosity of cystic fibrosis sputum in vitro by gelsolin" *Science* 263:969-971 (1994).

Welsh et al., "Cystic Fibrosis" *J. Clin. Invest.* 80:1523-1526 (Dec. 1987).

Yeates, D., "Mucus Rheology" *The Lung: Scientific Foundations*, R.G. Crystal et al., New York, NY:Raven Press pp. 197-203 (1991).

Zach et al., "Chest Physiotherapy—The Mechanical Approach to Antiinfective Therapy in Cystic Fibrosis" *Infection* 15(5):381-384 (1987).

TCCTGCACAG GCAGTGCCTT GAAGTGCTTC TTCAGAGACC TTTCTTCATA 50

GACTACTTTT TTTTCTTTAA GCAGCAAAAG GAGAAAATTG TCATCAAAGG 100

ATATTCCAGA TTCTTGACAG CATTCTCGTC ATCTCTGAGG ACATCACCAT 150

CATCTCAGG   ATG AGG GGC ATG AAG CTG CTG GGG GCG CTG 189
            Met Arg Gly Met Lys Leu Leu Gly Ala Leu
             1           5                      10

CTG GCA CTG GCG GCC CTA CTG CAG GGG GCC GTG TCC CTG 228
Leu Ala Leu Ala Ala Leu Leu Gln Gly Ala Val Ser Leu
             15                      20

AAG ATC GCA GCC TTC AAC ATC CAG ACA TTT GGG GAG ACC 267
Lys Ile Ala Ala Phe Asn Ile Gln Thr Phe Gly Glu Thr
 25                      30                      35

AAG ATG TCC AAT GCC ACC CTC GTC AGC TAC ATT GTG CAG 306
Lys Met Ser Asn Ala Thr Leu Val Ser Tyr Ile Val Gln
             40                      45

ATC CTG AGC CGC TAT GAC ATC GCC CTG GTC CAG GAG GTC 345
Ile Leu Ser Arg Tyr Asp Ile Ala Leu Val Gln Glu Val
 50                      55                      60

AGA GAC AGC CAC CTG ACT GCC GTG GGG AAG CTG CTG GAC 384
Arg Asp Ser His Leu Thr Ala Val Gly Lys Leu Leu Asp
             65                      70                      75

AAC CTC AAT CAG GAT GCA CCA GAC ACC TAT CAC TAC GTG 423
Asn Leu Asn Gln Asp Ala Pro Asp Thr Tyr His Tyr Val
             80                      85

GTC AGT GAG CCA CTG GGA CGG AAC AGC TAT AAG GAG CGC 462
Val Ser Glu Pro Leu Gly Arg Asn Ser Tyr Lys Glu Arg
 90                      95                      100

TAC CTG TTC GTG TAC AGG CCT GAC CAG GTG TCT GCG GTG 501
Tyr Leu Phe Val Tyr Arg Pro Asp Gln Val Ser Ala Val
             105                     110

GAC AGC TAC TAC TAC GAT GAT GGC TGC GAG CCC TGC GGG 540
Asp Ser Tyr Tyr Tyr Asp Asp Gly Cys Glu Pro Cys Gly
115                     120                     125

AAC GAC ACC TTC AAC CGA GAG CCA GCC ATT GTC AGG TTC 579
Asn Asp Thr Phe Asn Arg Glu Pro Ala Ile Val Arg Phe
             130                     135                     140

FIG. IA

```
TTC TCC CGG TTC ACA GAG GTC AGG GAG TTT GCC ATT GTT  618
Phe Ser Arg Phe Thr Glu Val Arg Glu Phe Ala Ile Val
            145                 150

CCC CTG CAT GCG GCC CCG GGG GAC GCA GTA GCC GAG ATC  657
Pro Leu His Ala Ala Pro Gly Asp Ala Val Ala Glu Ile
    155                 160                 165

GAC GCT CTC TAT GAC GTC TAC CTG GAT GTC CAA GAG AAA  696
Asp Ala Leu Tyr Asp Val Tyr Leu Asp Val Gln Glu Lys
            170                 175

TGG GGC TTG GAG GAC GTC ATG TTG ATG GGC GAC TTC AAT  735
Trp Gly Leu Glu Asp Val Met Leu Met Gly Asp Phe Asn
180             185                 190

GCG GGC TGC AGC TAT GTG AGA CCC TCC CAG TGG TCA TCC  774
Ala Gly Cys Ser Tyr Val Arg Pro Ser Gln Trp Ser Ser
        195                 200                 205

ATC CGC CTG TGG ACA AGC CCC ACC TTC CAG TGG CTG ATC  813
Ile Arg Leu Trp Thr Ser Pro Thr Phe Gln Trp Leu Ile
            210                 215

CCC GAC AGC GCT GAC ACC ACA GCT ACA CCC ACG CAC TGT  852
Pro Asp Ser Ala Asp Thr Thr Ala Thr Pro Thr His Cys
    220                 225                 230

GCC TAT GAC AGG ATC GTG GTT GCA GGG ATG CTG CTC CGA  891
Ala Tyr Asp Arg Ile Val Val Ala Gly Met Leu Leu Arg
            235                 240

GGC GCC GTT GTT CCC GAC TCG GCT CTT CCC TTT AAC TTC  930
Gly Ala Val Val Pro Asp Ser Ala Leu Pro Phe Asn Phe
245             250                 255

CAG GCT GCC TAT GGC CTG AGT GAC CAA CTG GCC CAA GCC  969
Gln Ala Ala Tyr Gly Leu Ser Asp Gln Leu Ala Gln Ala
        260                 265                 270

ATC AGT GAC CAC TAT CCA GTG GAG GTG ATG CTG AAG TGAGC 1010
Ile Ser Asp His Tyr Pro Val Glu Val Met Leu Lys
            275                 280     282

AGCCCCTCCC CACACCAGTT GAACTGCAG 1039
```

FIG. 1B

| Sputum sample # | Total DNA (mg/mL) | % Dry weight (w/w) | Elasticity[1] | | Compaction assay[2] | |
|---|---|---|---|---|---|---|
| | | | diluent | rhDNase | diluent | rhDNase |
| 1 | 9.2 ± 0.5 | 11.2 | 77.0 | 18.1 | 57.3 | 42.7 |
| 2 | 13.0 ± 0.3 | 9.8 | 55.2 | 28.3 | 70.2 | 53.3 |
| 3 | 10.8 ± 0.8 | 10.6 | 357.8 | 70.2 | 94.4 | 64.8 |
| 4 | 4.8 ± 1.1 | 8.3 | 57.1 | 6.2 | 63.0 | 25.7 |
| 5 | 2.8 ± 0.0 | 9.1 | 35.9 | 22.2 | 93.4 | 50.9 |
| 6 | 11.5 ± 3.8 | 11.0 | 314.7 | 36.4 | 77.4 | 46.5 |
| mean | 8.7 | 10.0 | 149.6 | 30.2 | 76.0 | 47.3 |
| std. dev | 4.0 | 1.1 | 145.8 | 22.0 | 15.5 | 13.0 |

[1] elasticity measurements taken at 20% strain

[2] percent pellet height, taken as the height of the pellet divided by the total height x 100.

FIG. 5

| SAMPLE NUMBER | DILUENT TREATED | | rhDNase TREATED | |
|---|---|---|---|---|
| | $[DNA]_s$ | $[DNA]_p$ | $[DNA]_s$ | $[DNA]_p$ |
| 1 | 4.2 | 12.2 | 7.0 | 12.8 |
| 2 | 5.6 | 18.2 | 8.1 | 16.5 |
| 3 | 2.9 | 12.3 | 9.9 | 10.4 |
| 4 | 0.48 | 9.8 | 3.5 | 8.1 |
| 5 | 1.6 | 3.7 | 2.2 | 4.3 |
| 6 | 0.8 | 21.9 | 6.0 | 12.8 |

$[DNA]_s$: DNA concentration (mg/mL) in the supernatant.

$[DNA]_p$: DNA concentration (mg/mL) in the pellet.

FIG. 6

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
       (A) LENGTH: 1039 bases
       (B) TYPE: nucleic acid
       (C) STRANDEDNESS: single
       (D) TOPOLOGY: linear (xi) SEQUENCE DESCRIPTION: SEQ ID NO: 1:

```
TCCTGCACAG GCAGTGCCTT GAAGTGCTTC TTCAGAGACC TTTCTTCATA           50

GACTACTTTT TTTTCTTTAA GCAGCAAAAG GAGAAAATTG TCATCAAAGG          100

ATATTCCAGA TTCTTGACAG CATTCTCGTC ATCTCTGAGG ACATCACCAT          150

CATCTCAGG   ATG AGG GGC ATG AAG CTG CTG GGG GCG CTG             189
            Met Arg Gly Met Lys Leu Leu Gly Ala Leu
              1               5                  10

CTG GCA CTG GCG GCC CTA CTG CAG GGG GCC GTG TCC CTG             228
Leu Ala Leu Ala Ala Leu Leu Gln Gly Ala Val Ser Leu
             15                  20

AAG ATC GCA GCC TTC AAC ATC CAG ACA TTT GGG GAG ACC             267
Lys Ile Ala Ala Phe Asn Ile Gln Thr Phe Gly Glu Thr
  25                  30                      35

AAG ATG TCC AAT GCC ACC CTC GTC AGC TAC ATT GTG CAG             306
Lys Met Ser Asn Ala Thr Leu Val Ser Tyr Ile Val Gln
```

```
                    40                    45
ATC CTG AGC CGC TAT GAC ATC GCC CTG GTC CAG GAG GTC             345
Ile Leu Ser Arg Tyr Asp Ile Ala Leu Val Gln Glu Val
 50              55                  60

AGA GAC AGC CAC CTG ACT GCC GTG GGG AAG CTG CTG GAC             384
Arg Asp Ser His Leu Thr Ala Val Gly Lys Leu Leu Asp
             65                  70                  75

AAC CTC AAT CAG GAT GCA CCA GAC ACC TAT CAC TAC GTG             423
Asn Leu Asn Gln Asp Ala Pro Asp Thr Tyr His Tyr Val
                 80                  85

GTC AGT GAG CCA CTG GGA CGG AAC AGC TAT AAG GAG CGC             462
Val Ser Glu Pro Leu Gly Arg Asn Ser Tyr Lys Glu Arg
     90                  95                 100

TAC CTG TTC GTG TAC AGG CCT GAC CAG GTG TCT GCG GTG             501
Tyr Leu Phe Val Tyr Arg Pro Asp Gln Val Ser Ala Val
                105                 110

GAC AGC TAC TAC TAC GAT GAT GGC TGC GAG CCC TGC GGG             540
Asp Ser Tyr Tyr Tyr Asp Asp Gly Cys Glu Pro Cys Gly
115                 120                 125

AAC GAC ACC TTC AAC CGA GAG CCA GCC ATT GTC AGG TTC             579
Asn Asp Thr Phe Asn Arg Glu Pro Ala Ile Val Arg Phe
        130                 135                 140

TTC TCC CGG TTC ACA GAG GTC AGG GAG TTT GCC ATT GTT             618
Phe Ser Arg Phe Thr Glu Val Arg Glu Phe Ala Ile Val
                145                 150

CCC CTG CAT GCG GCC CCG GGG GAC GCA GTA GCC GAG ATC             657
Pro Leu His Ala Ala Pro Gly Asp Ala Val Ala Glu Ile
        155                 160                 165

GAC GCT CTC TAT GAC GTC TAC CTG GAT GTC CAA GAG AAA             696
Asp Ala Leu Tyr Asp Val Tyr Leu Asp Val Gln Glu Lys
                170                 175

TGG GGC TTG GAG GAC GTC ATG TTG ATG GGC GAC TTC AAT             735
Trp Gly Leu Glu Asp Val Met Leu Met Gly Asp Phe Asn
180                 185                 190

GCG GGC TGC AGC TAT GTG AGA CCC TCC CAG TGG TCA TCC             774
Ala Gly Cys Ser Tyr Val Arg Pro Ser Gln Trp Ser Ser
        195                 200                 205

ATC CGC CTG TGG ACA AGC CCC ACC TTC CAG TGG CTG ATC             813
Ile Arg Leu Trp Thr Ser Pro Thr Phe Gln Trp Leu Ile
                210                 215

CCC GAC AGC GCT GAC ACC ACA GCT ACA CCC ACG CAC TGT             852
Pro Asp Ser Ala Asp Thr Thr Ala Thr Pro Thr His Cys
        220                 225                 230

GCC TAT GAC AGG ATC GTG GTT GCA GGG ATG CTG CTC CGA             891
Ala Tyr Asp Arg Ile Val Val Ala Gly Met Leu Leu Arg
                235                 240

GGC GCC GTT GTT CCC GAC TCG GCT CTT CCC TTT AAC TTC             930
Gly Ala Val Val Pro Asp Ser Ala Leu Pro Phe Asn Phe
245                 250                 255

CAG GCT GCC TAT GGC CTG AGT GAC CAA CTG GCC CAA GCC             969
Gln Ala Ala Tyr Gly Leu Ser Asp Gln Leu Ala Gln Ala
        260                 265                 270

ATC AGT GAC CAC TAT CCA GTG GAG GTG ATG CTG AAG TGAGC          1010
Ile Ser Asp His Tyr Pro Val Glu Val Met Leu Lys
                275                 280     282

AGCCCCTCCC CACACCAGTT GAACTGCAG                                1039
```

COMPACTION ASSAY FOR ASSESSMENT OF RESPIRATORY DISEASE THERAPY

This application is a continuation application Ser. No. 10/162,951, filed Jun. 4, 2002, now abandoned, which is a continuation of application Ser. No. 09/771,078, filed Jan. 25, 2001, now abandoned, which is a continuation of Ser. No. 08/840,441, filed Apr. 1, 1997, now abandoned, which is a continuation application of Ser. No. 08/539,468, filed Oct. 5, 1995, now abandoned, which is a file wrapper continuation application of Ser. No. 08/355,418, filed Dec. 13, 1994, now abandoned, which is a file wrapper continuation application of Ser. No. 08/132,681, filed Oct. 6, 1993, now abandoned, which is a file wrapper continuation application of Ser. No. 07/971,019, filed Nov. 2, 1992, now abandoned, the entire disclosures of which are hereby incorporated by reference.

FIELD OF THE INVENTION

The present invention relates to an assay that measures the compaction of sputum samples of mammalian patients subject to respiratory disease associated with infected airway secretions.

The present invention relates to a compaction assay that measures the potential of a therapeutic to improve lung function in a patient subject to respiratory disease.

The present invention specifically relates to a compaction assay that is predictive of DNase therapeutic efficacy in a population of patients.

DESCRIPTION OF RELATED ART

Respiratory Disease

Lung secretions are complex non homogenous materials that form a viscous hydrophilic gel. These secretions play an important role in the normal functioning of the respiratory airways. Respiratory diseases associated with infected airway secretions such as Cystic Fibrosis (CF), Bronchitis, and Pneumonia are characterized by purulent secretions that play a major part in the respiratory dysfunction associated with respiratory disease.

The viscosity of uninfected lung secretions has been attributed to mucus glycoproteins, whereas the viscosity of infected or purulent lung secretions has been attributed to mucus proteins and DNA (Shak et al., *PNAS* 87:9188–9192 [1990]) and glycoproteins, DNA, proteins, lipids and cations, (Yeates, D B, *The Lung: Scientific Foundations*, editor Crystal et al., publisher Raven Press pg 197–203 [1991]).

Cystic fibrosis (CF) is a genetic disease characterized by a defect in secretory epithelia involved with electrogenic chloride transport and is the most common lethal genetic disease among Caucasians, being observed in approximately one in 2,500 live births (Boat et al., *The Metabolic Basis of Inherited Disease* editors Scriver et al., publisher McGraw Hill, pgs. 2649–2860 [1989]). Disturbances in the function of secretory epithelia result in several abnormalities including reduced pancreatic enzyme secretion, malabsorption in the gastrointesxtinal tract, and excessive secretion of bronchial mucus (Kerem et al. *New England Journal of Medicine*, 323: 1517–1522 [1990]). These excessive bronchial secretions provide an environment that supports chronic lung infections by opportunistic pathogens such as *Pseudomonas aeruginosa* (George, R H *Arch Dis Child*, 62:438–439 [1987]). Large numbers of inflammatory leukocytes enter these infection sites and lyse after a short time, releasing their nuclear deoxyribonucleic acid (DNA) into the bronchial secretions. Extremely purulent secretions, which have been shown to contain as much as 15 mg/ml DNA (Matthews et al., *Am Rev Respir Dis* 88:199–204 [1963]), become too thick for the CF patient to clear; resulting in respiratory distress and progressive lung destruction (Welsh et al., *J Clin Invest* 80:1523–1526 [1987]).

Pneumonia is characterized by inflammation of the lung parenchyma. Most cases of pneumonia are due to infection by bacteria or viruses, a few to inhalation of chemicals or trauma to the chest wall, and a small minority to rickettsias, fungi, and yeasts. The distribution of inflammation may be lobar, segmental, or lobular. One clinical manifestation of pneumonia is the presence of purulent secretions in the respiratory airways.

Bronchitis is characterized by inflammation of the mucus membrane of the bronchial tubes. There are many forms of bronchitis, including chronic bronchitis, hemaorrhagic bronchitis, fibrinous bronchitis, capillary bronchitis, and asthmatic bronchitis. Chronic bronchitis is a condition of the bronchial tree characterized by cough, hypersecretion of mucus, and expectoration of sputum over a long period of time, associated with increased vulnerability to bronchial infection. An increase in the viscosity of purulent secretions is correlated with difficulty in expectoration in patients with chronic bronchitis (Dulfano et al., *Am. Rev. Respir. Dis.* 104:88–98 [1971]).

Several approaches have been taken in the past to reduce the viscoelastic nature of purulent tracheobronchial secretions of mammalian patients subject to respiratory disease associated with infected airway secretions, hopefully to improve clearance of this material by the patient. Therapies such as the inhalation of water (Rosenbluth et al., *Archives of Disease in Childhood* 49: pg 606–610 [1974]) and the use of mucolytics such as n-acetylcysteine (Mucomyst®) have not been successful.

Bovine pancreatic DNase I (Dornase) was shown to be effective in the treatment of pneumonia (Clifton, et al., *Cancer* (14):414–420 [1961]) but its use fell from favor due to irritation problems found to occur in humans using this bovine protein (Shak et al., *PNAS* 87: 9188 [1990]). Recently, Hubbard et al. (*NEJM* 326:812–815 [1992]) and Aitken et al., JAMA vol. 267 pg. 1947–1951 [1992]) reported that human DNase cleaved high-molecular-weight DNA in purulent secretions in the airways, thereby reducing the viscoelasticity of the purulent secretions and improving lung function. Human DNase has also been indicated in the treatment of chronic bronchitis bronchiectasis, sinus infections and other respiratory disease (PCT/US89/05744).

Other therapeutics such as, anti-neutrophil elastase agents and secretory leucoprotease inhibitor are potentially promising new therapies for the treatment of CF (Mulherin et al., *Dig Dis* 10(1) pg 29–37 [1992]). Antibiotic therapy is indicated for the treatment of chronic respiratory tract infections associated with CF and other respiratory disease (Mulherin et al., *Ir J Med Sci* 160(6) pg 173–175 [1991] and de Montalembert et al., *Ann Pediatr* 38(8) p 523–528 [1991]). Chest physiotherapy has also been indicated as a mechanical approach to antiinfective therapy in cystic fibrosis (Zach et al., *Infection* 15(5) pg. 381–384 [1987]) and asthma, chronic bronchitis, and bronchiectasis (Eid, et al., Respir Care 36(4) pg. 270–282 [1991]).

DNase

DNase is a phosphodiesterase capable of hydrolyzing polydeoxyribonucleic acid. It acts extensively and nonspecifically to degrade DNA and in this regard is distinguished from the relatively limited and sequence-specific restriction endonucleases. DNase I has a pH optimum near neutrality, an obligatory requirement for divalent cations, and produces 5' phosphate nucleotides on hydrolysis of DNA. DNase II exhibits an acid pH optimum, can be activated by divalent cations and produces 3'-phosphate nucleotides on hydrolysis of DNA. Multiple molecular forms of DNase I and DNase II are known.

DNase has a number of known utilities, and has been used for therapeutic purposes. Its principal therapeutic use has been to reduce the viscoelastic properties of infected airway secretions in respiratory diseases, such as cystic fibrosis, pneumonia, and bronchitis, thereby aiding in the clearing of respiratory airways and improvement of lung function.

Bovine DNase A, B, C, and D were purified and completely sequenced as early as 1973. Bovine pancreatic DNase has been sold under the tradename Dornavac (Merck), and was used in the treatment of patients subject to pneumonia and CF. This product was withdrawn from the market after clinicians observed serious complications from its use (Raskin, *Am. Rev. Respir. Dis.* 98:597–598 [1968]).

Human DNase I was cloned and expressed by Shak, et al., Supra who reported that catalytic amounts of recombinant human DNase (rhDNase) greatly reduced the viscosity of purulent cystic fibrosis sputum, transforming it from a non-flowing viscous gel to a flowing liquid, thereby increasing sputum clearance. Hubbard et al., supra and Aiken et al. (*JAMA* 267:1947–1951 [1992]) reported improved lung function in CF patients upon treatment with aerosolized rhDNase.

Effect of Mucus Rheology on Respiratory Airways

Respiratory secretions, such as mucus, play an important role in the normal functioning of the respiratory airways. These respiratory secretions protect the airways against airborne microorganisms and other foreign particles by providing a continuous flow, or transport, of secretions under the propelling action of ciliated epithelium. This transport helps in clearing the trapped particles and microorganisms in the mucus lining the airways. The viscoelastic gel properties of normal mucus are critical for effective mucociliary transport (Yeates et al., Supra).

Patients subject to respiratory disease characterized by infected airway secretions have been shown to secrete excessive amounts of purulent secretions having abnormal viscoelastic properties. There is variability in the viscoelasticity of infected sputum dependent upon the respiratory disease type, severity, and duration that makes treatment regimes unpredictable.

King et al. (*Rheology* 24: 589–597 [1987]) show an inverse relationship between viscoelasticity and ciliary transport; the greater the viscoelasticity the less the ciliary transport. Impaired ciliary transport can lead to lung obstruction of airways by infected secretions that can cause respiratory distress, and in some cases, can lead to respiratory failure and death.

Researchers have attempted without success to find a correlation between in vitro and in vivo assessment of the rheologic properties of sputum. Reid et al ("Rheology-Relation to the Composition of Sputum" *Scandinavian Journal of Respiratory Diseases* Publisher: Munksgaard International Publishers Vol 103 Suppl. pg 27–35 [1974]) state that in vitro assessment of shear rates of sputum cannot be used to assess the rheological properties of sputum in vivo. Rosenbluth et al. (*Archives of Disease in Childhood*, 49:606 [1974]) demonstrate that although increasing the water content of CF sputum in vitro reduces viscosity, mist therapy did not influence sputum viscosity or volume in patients with CF.

Measurements of the Rheological Properties of Sputum

Relevant rheological measurements of the sputum of patients subject to respiratory disease can be difficult to obtain with a single rheological method. In fact, results from one technique are rarely comparable to results obtained by other techniques due to the inherent variability of the viscoelasticity of patient sputum samples and the non-Newtonian characteristics of sputum where the values of viscosity and elasticity depend on the method of analysis.

Several types of instruments have been used to study the rheological properties of mucus, including the dynamic cone and plate viscometer, the capillary rheometer, the oscillating magnetic ball micro-rheometer, and the magnetic rheometer. These instruments measure dynamic moduli related to viscosity and elasticity.

The dynamic cone and plate viscometer is one of the least destructive of these methods and can yield information simultaneously about both viscosity and elasticity of a specimen; however this method requires using relatively large volumes of sputum. The capillary rheometer, while requiring small sample volumes, has several limitations, including problems with sample handling. The magnetic micro-rheometer does not work satisfactorily for materials that are highly heterogenous such as sputum, because the particles' motion is often stopped when it moves into an area of higher viscosity.

Yeates et al. Supra, caution that comparisons of Theological values derived with different instruments need to be made with discretion, because each is dependent on the application of different Theological principles.

Many methods used to obtain Theological measurements are destructive, irrevocably altering the physical nature of the sputum during storage or data collection. This is true of freezing and the use of devices such as the static cone and plate rheometer, frequently used for viscosity determinations. Many instruments, including the dynamic cone and plate rheometer, are very expensive and require a trained technician to operate the instrument and to interpret the resulting data.

Until the present invention there was no simple, validated or standardized in vitro rheological assay to assess the potential of a therapeutic to improve lung function in a patient subject to respiratory disease. Until the present invention there was no simple, validated or standardized in vitro rheological assay to measure respiratory disease severity as a function of viscoelasticity. Until the present invention there was no method for assessing the therapeutic efficacy of rhDNase treatment on mammalian patients subject to respiratory disease.

The compaction assay of the present invention is based upon the change in sputum compactability in a centrifugal field following in vitro DNase treatment of sputum. The extent of sputum compactability, as measured by centrifugal pellet size, is related to the content of large molecular weight DNA. The greater the amount of large molecular weight DNA in a sputum sample, the more resistance to compaction. DNase acts to hydrolyze the large molecular weight DNA present in purulent sputum thereby increasing the centrifugal compactability of an in vitro DNase treated sample. The greater the increase in compactability of an in vitro DNase treated sputum sample from a patient, the greater the improvement in patient lung function found with in vivo rhDNase treatment.

There exists a need for a simple and rapid standardized assay to assess the ability of a therapeutic to improve lung function in a population of patients. This need exists in any patient population subject to respiratory disease characterized by infected airway secretions.

In many instances, it would be desirable to assess the severity of respiratory disease in a mammalian patient in order to determine effective dosage regimens of therapeutics useful in the treatment of respiratory disease. It would be particularly desirable to have a rapid and simple in vitro assay predictive of in vivo efficacy of DNase therapy in a population of patients in need of DNase therapy.

Accordingly, it is an object of the present invention to provide a rapid and simple standardized assay that can assess the potential of a therapeutic to improve lung function in a population of patients.

It is an object of the present invention to provide a rapid and simple in vitro assay to assess the severity of respiratory disease in a mammalian patient in order to determine effective dosage regimens of therapeutics useful in the treatment of respiratory disease. It is a related object of the present invention to provide an in vitro assay that is predictive of in vivo efficacy of DNase therapy in a population of patients in need of DNase therapy.

These and other objects of the present invention will become apparent to those skilled in the art.

SUMMARY OF INVENTION

The present invention is based on the unexpected experimental finding that in vitro measurements of viscoelasticity obtained by the compaction assay are predictive of the severity of respiratory disease in a mammalian patient and predictive of in vivo efficacy of therapeutics useful in the treatment of respiratory disease in improving lung function.

The objects of the present invention are accomplished by providing a method for measuring the compaction of a sputum sample from a mammalian patient subject to respiratory disease associated with infected airway secretions, comprising obtaining a sputum sample from the mammalian patient, centrifuging said sputum sample until fractionated into supernatant and pellet phases, and measuring the pellet.

In one embodiment, the sputum sample is from a mammalian patient subject to cystic fibrosis. In another embodiment, the sputum sample is from a mammalian patient subject to bronchitis.

In yet another embodiment, the present invention provides for a method of measuring the compaction of a mammalian patient sputum sample treated in vitro with a therapeutic, comprising obtaining a sputum sample from the mammalian patient, adding therapeutic to the sputum sample, centrifuging said sputum sample until fractionated into supernatant and pellet phases, and measuring the pellet.

In one embodiment, the therapeutic is human DNase. In another embodiment the therapeutic is an antibiotic useful in the treatment of respiratory disease.

In yet another embodiment of the present invention, a method is provided for measuring the compaction of a DNase treated sputum sample of a mammalian patient in need of DNase therapy comprising, obtaining a sputum sample from the mammalian patient, adding DNase to the sputum sample, centrifuging the DNase treated sputum sample until fractionated into supernatant and pellet phases, and measuring the pellet.

In another embodiment, the DNase is human DNase in a concentration of at least 1 µg DNase/mL sputum.

BRIEF DESCRIPTION OF THE FIGURES

FIG. 1 shows the nucleotide and amino acid sequences of DNase.

FIG. 5 shows the physical properties of six purulent samples.

FIG. 6 shows the extent of DNA detected in the pellet and supernatant fractions of six samples following addition of diluent or rhDNase.

DESCRIPTION OF THE PREFERRED EMBODIMENTS

Figure 2:
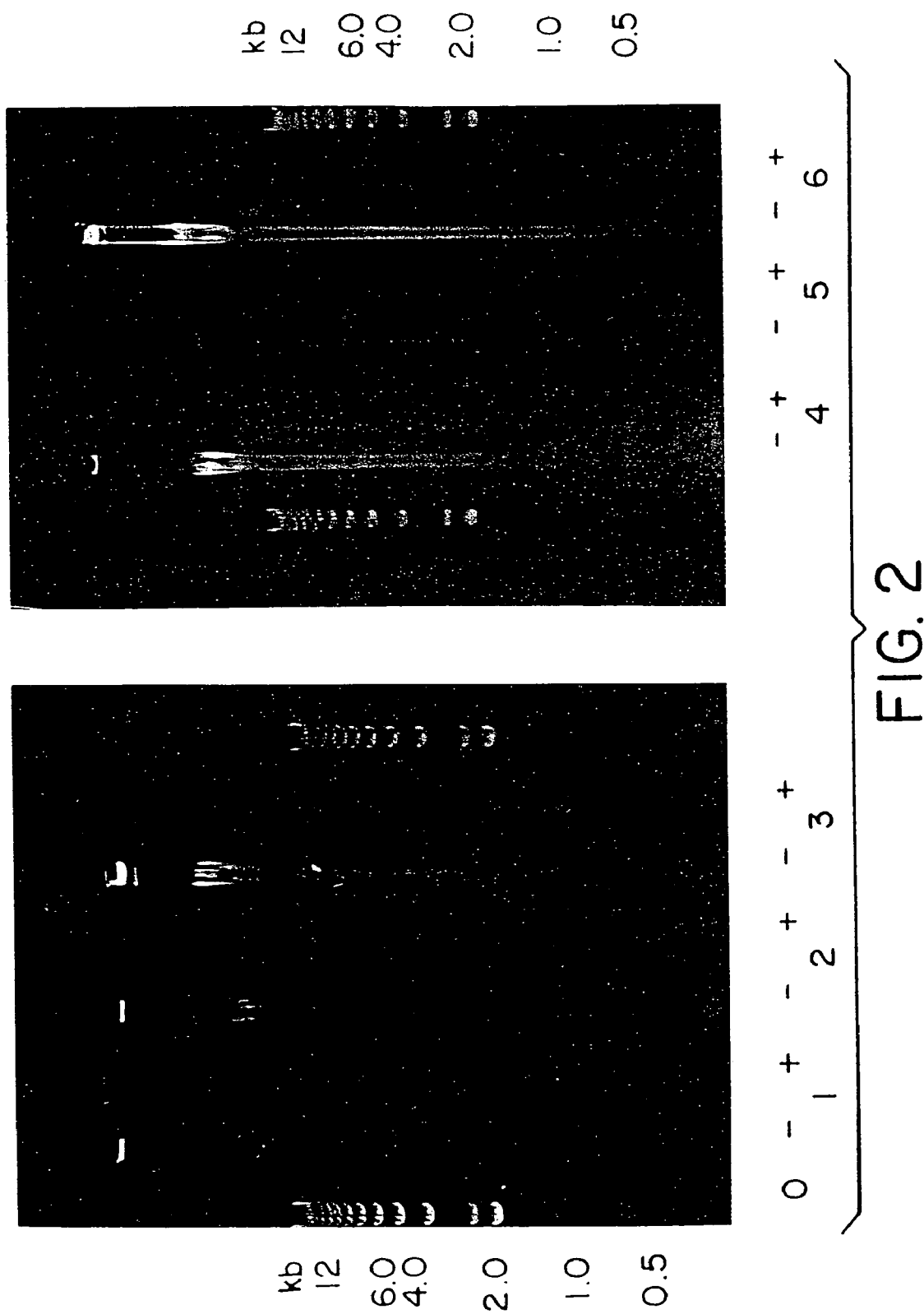
FIG. 2 is an agarose gel electrophoresis study of DNA size within sputum samples. Sputum samples were prepared by treatment with either diluent, the minus lanes, or rhDNase, the plus lanes, and electrophoresed into a 0.5% agarose gel. 1

The use of the term "compaction" as used herein refers to the resistance to deformation of a sputum sample upon centrifugation and is a direct function of sample viscoelasticity. The more viscoelastic a sample, the less compactability the sample will have upon centrifugation as measured by centrifugal pellet size. Compaction assay results are useful in a clinical setting to assess respiratory disease severity, as a function of sputum viscoelasticity, and to assess the potential of therapeutics in improving lung function in mammalian patients subject to respiratory disease.

The therapeutic efficacy of DNase in improving lung function in a mammalian patient in need of DNase therapy can be predicted by assaying compactability of the mammalian patient sputum sample following in vitro treatment with DNase. If centrifugal pellet size decreases upon in vitro DNase treatment, it is predicted that treatment of the mammalian patient with human DNase will improve lung function. The reduction of pellet size after DNase treatment is due to the hydrolysis of long chain DNA to shorter chains. The subsequent release of the short chain DNA into the supernatant results in increased pellet compaction and increased supernatant volume. This effect can be quantified and used as an indicator of the extent of viscoelasticity change after in vivo rhDNase treatment. Those patients in need of DNase treatment are predicted to be responsive to DNase therapy if in vitro rhDNase treatment increases compaction of the patient's sputum sample.

Centrifugation of an untreated sputum sample from a mammalian patient in need of DNase treatment yields a sample having a DNA concentration greater in the centrifugal pellet than in the remaining supernatant. Because of the dehydrated condition of the sputum of mammalian patients in need of DNase therapy, centrifugation at 10,000×g alone does not always produce a supernatant phase. It is often necessary to add diluent to the sputum sample in order to obtain centrifugal fractionation of the sample into two phases and the amount of diluent added should be the same for all samples being tested. If a positive displacement pipette is used for measuring the sputum sample to be tested, it is preferable to add diluent to the sputum sample in a volume equaling 50% of the measured sample volume to insure at least a 20% supernatant volume upon centrifugation. If the sputum sample is measured gravimetrically it is preferable to add diluent to the sputum sample in a volume equaling 50% of the exact sputum weight to yield at least a 20% supernatant volume upon centrifugation. For example, if the exact sputum volume as measured by a positive displacement pipette is 100 microliters (μl), then addition of 50 μl of diluent is typically necessary to yield at least a 20% supernatant volume upon centrifugation or for example, if the exact sputum sample weight is 100 milligrams (mg), then addition of 50 μl of diluent is typically necessary to insure at least a 20% supernatant volume upon centrifugation. Typically, a Mettler analytical balance is used for measuring sputum sample weight. Unless a positive displacement pipette is used for measuring the sputum sample volume, the addition of diluent volume based on sputum sample weight is necessary due to the presence of air bubbles and mucus plugs in the sputum sample which can affect volume measurements. After the addition of diluent or DNase and subsequent centrifugation, the resulting supernatant is neither elastic nor viscous, however, the remaining pellet is quite solid or elastic. The remaining pellet phase contains the components that contribute to the elasticity of whole sputum.

DNase is defined as a polypeptide having the amino acid sequence of FIG. 1, together with amino acid sequence variants thereof which retain the qualitative enzymatic activity of DNase. As used herein the term "DNase" refers variously to all forms of human and non-human animal DNase as are known to be biologically active in accepted DNase assays, such as ELISA, RIA, hydrolysis of $^{32}$P-labeled DNA, or PAGE electrophoresis, as described in PCT/US89/05744 or agar plate DNase assay (Smith et al., *Applied Microbiology* 18:991 [1969]) and is meant to include DNase in a mature, pro, or met form, whether obtained from natural source, chemically synthesized or produced by techniques of recombinant DNA technology.

A complete description of the preparation of recombinant human DNase (rhDNase) including its cDNA and amino acid sequences and expression is shown in Shak et al., *PNAS* 87:9188–9192 [1990]) and PCT/US89/05744, specifically incorporated by reference. Non-human animal DNase, including bovine, porcine, and ovine are, for example, disclosed in Liao et al. (*J. Biol. Chem.* 248:1489 [1973]); Salnikow et al. (*J. Biol. Chem.* 248: 1499 [1973]); Liao et al. (*J. Biol. Chem.* 249:2354 [1973]); Paudel et al. (*J. Biol. Chem.* 261: 16006 [1986]); and Paudel et al. (*J. Biol. Chem.* 261: 16012 [1986]).

The term DNase includes variously glycosylated forms and other variants and derivatives of such DNases, whether known in the art or becoming available in the future. Examples of such variants are alleles, and the products of site directed mutagenesis in which residues are deleted, inserted and/or substituted. Preferably, the variants are not immunogenic in humans. Variants may possess greater enzymatic activity, improved solubility, or may be expressed at higher levels by host cells.

DNA encoding human DNase is synthesized by in vitro methods or is obtained readily from human pancreatic cDNA libraries as described in Shak et al., Supra. Expression of rhDNase is described in Shak et al., Supra and PCT/US89/05744.

Human DNase is placed into therapeutic formulations together with required cofactors, and optionally is administered in the same fashion as has been the case for animal DNase such as bovine pancreatic DNase. The preferred formulation for human DNase is a buffered or unbuffered solution, and is preferably an isotonic salt solution such as 150 mM sodium chloride, containing 1.0 mM calcium at pH 7. The concentration of sodium chloride may range from 75 mM to 250 mM. The concentration of calcium may range from 0.01 to 0.05 mM, and other divalent cations that stabilize DNase may be included or substituted for calcium. The pH may range from 5.5–9.0, and buffers compatible with the included divalent cation may also be utilized. These solutions are particularly adaptable for use in commercially-available nebulizers including jet nebulizers and ultrasonic nebulizers useful for administration, for example directly into the airways or lungs of a patient subject to respiratory disease associated with infected airway secretions. The formulation may be lyopholized powder, also containing calcium.

Commercially available nebulizers for liquid formulations, including jet nebulizers and ultrasonic nebulizers are useful for administration. Liquid formulations may be directly nebulized and lyophilized powder nebulized after reconstruction. Alternatively, DNase may be aerosolized using a fluorocarbon formulation and a metered dose inhaler, or inhaled as a lyophilized and milled powder.

Purified DNase is employed for enzymatic alteration of the viscoelasticity of sputum. Human DNase is particularly useful for the treatment of patients with pulmonary disease who have abnormal, viscous or inspissated purulent secretions in conditions such as acute or chronic broncopulmonary disease (infectious pneumonia, bronchitis or tracheobronchitis, bronchiectrasis, cystic fibrosis, asthma, TB or fungal infections), atelectasis due to tracheal or bronchial impaction, and complications of tracheostomy. For such therapies a solution or finely divided dry preparation of human DNase is instilled in conventional fashion into the bronchi, e.g. by aerosolization of a solution of DNase.

Chemical action of in vitro rhDNase treatment of sputum samples can be verified by using agarose gel electrophoresis following the procedure of Shak et al., Supra and PCT/US89/05744.

DNase may also be administered along with other pharmacologic agents used to treat the conditions listed above such as antibiotics, bronchodilators, anti-inflammatory agents, and mucolytics e.g. n-acetylcysteine.

Mammalian patients in need of DNase therapy are those patients subject to respiratory disease characterized by infected airway secretions.

The therapeutically effective amount of DNase used in the treatment of human patients subject to respiratory disease associated with infected airway secretions is a dosage of from about 1 μg to about 100 mg of human DNase per kilogram of body weight of the patient, administered with pharmaceutical compositions, as described herein. The therapeutically effective amount of human DNase will depend, for example upon the therapeutic objectives, the route of administration, and the condition of the patient. Accordingly, it will be necessary for the therapist to titer the dosage and modify the route of administration as required to obtain the optimal therapeutic effect.

DNA in Sputum of Patients Subject to Respiratory Disease

In a number of respiratory diseases the deoxyribonucleic acid (DNA) content of sputum increases with the degree of purulence (Picot et al., *Thorax,* 33: 235–242 [1978]). This is particularly the case in CF where high levels of infection are associated with increased levels of sputum DNA (Carswell et al., *Eur. J. Respir Dis* 65: 53–57 [1984]). There is inherent variability in the properties of DNA obtained from the sputum samples of patients subject to respiratory disease.

DNA influences the viscoelasticity of sputum through the interaction with other components of sputum including the mucus glycoproteins.

The DNA present in the sputum of patients subject to respiratory disease originates from either infecting organisms or from the patient's own cells (Lethem, et al., *Eur. Respir J.,* 3:19–23 [1990]). If the host cells are the major contributor to total sputum DNA, this is a reflection of the content of leukocytes and epithelial cells present due to inflammation. Lethem, et al. Supra report that the DNA co-purifying with mucus glycoproteins is human in origin which suggests that it is the inflammatory processes resulting from infection, rather than the infection itself which are the source of the DNA in CF sputum.

Use of Antibiotics in Respiratory Disease

The presence of purulent respiratory secretions in the airways of patients subject to respiratory disease makes an excellent growth medium for microorganisms, and pulmonary infections are commonplace despite normal host defense mechanisms. The use of antibiotics is indicated for these infections.

The three most common bacterial pathogens isolated from the sputum of cystic fibrosis (CF) patients are *Staphylococcus aureus, Pseudomonas aeruginosa,* and *Hemophilus influenzae. Proteus* and *Klebsiela* species are observed much less frequently. The presence of these bacteria is believed to be responsible for some of the destructive changes in the lungs of cystic fibrosis patients.

Chronic sinusitis is also found in CF and may result from obstruction of the sinus ducts which prevents drainage and is not related to the underlying lung disease. The bacteria generally isolated in these cases of sinusititis include *P. aeruginosa, H. influenzae,* streptococci, and anaerobes.

Although the use of antibiotics in CF is both controversial and fraught with difficulty (In *Pharmacotherapy: a Pathophysiologic Approach* Editors: DiPiro and Talbert et al., Publisher Elsevier New York, pg 836–843 [1989]), most clinicians do treat pulmonary infections associated with CF with antibiotics. Specific therapy is directed at proven or likely pathogens such as *Pseudomonas aeruginosa* and *Staphylococcus aureus,* and usually includes an aminoglycoside and an extended-spectrum penicillin. While complete eradication of the pathogen is a practical endpoint in antibiotic therapy, the total eradication of *Pseudomonas aeruginosa* is infrequent and transient. Therefor a practical endpoint for the use of antibiotics is a return to the preexacerbation clinical status or pulmonary function status.

Another problem with antibiotic use in CF is altered pharmacokinetic disposition of some antibiotics in most CF patients. Many CF patients have increased total body clearance for many antibiotics and therefore higher doses of these agents may be necessary to produce therapeutic concentrations. Unfortunately, these alterations in pharmacokinetics are not consistent or predictable. Upward adjustments in dosage should be made with some degree of caution and should be followed with further determination of serum concentrations.

Although controversy exists surrounding the use of antibiotics in chronic bronchitis (In *Pharmacotherapy: a Pathophysiologic Approach* Editors: DiPiro and Talbert et al., Publisher Elsevier New York, pg. 1092–1095 [1989]), the antibiotics most frequently selected in the treatment of chronic bronchitis (ampicillin, tetracycline, chloramphenicol, trimethoprim-sulfamethoxazole) possess in vitro activity against the common sputum isolate; *H. influenzae, S. pneumoniae,* and *M. pneumoniae.*

Numerous antibiotics are available for the treatment of pneumonia. Once a causative pathogen(s) has been identified, an antibiotic regimen can be targeted to the particular pathogen(s) identified. Antibiotics useful in the treatment of pneumonia include but are not limited to erythromycin, ampicillin, penicillin, semi-synthetic penicillin, tetracycline, cefuroxime, cephalosporin, clindamycin, aminoglycoside, and ticarcillin. A complete listing of antimicrobial agents for specifically directed therapy can be found in *The Medical Letter Handbook of Antimicrobial Therapy* (In *Pharmacotherapy: a Pathophysiologic Approach* Editors: DiPiro and Talbert et al., Publisher Elsevier New York, pg. 1100–1105 [1989]).

The term "rheology" and grammatical derivatives thereof as used herein refer to the deformation and flow properties of a substance. With a viscoelastic substance such as sputum the flow properties are based on viscosity and elasticty.

Several types of rheometers have been used to study the rheological properties of mucus. Rotational rheometers have either a coaxial-cylinder (Davis "Rheological Examination of Sputum and Saliva and the Effects of Drugs, In: Gabelnick H L, Litt M, eds. *Rheology of Biological Systems.* Springfield, Ill.: Charles C Thomas pub pg. 158–193 [1973]), a cone and plate (Mitchell-Heggs "Physical Properties of Microliter Quantities of Normal Mucus" In: Elstein and Parke Eds. *Mucus in Health and Disease. Advances in Experimental Medicine and Biology* vol 89. New York: Plenum Press, pg. 203–215 [1977]), or a parallel-disk sensor system (Puchelle Biorheology 21:265–272 [1984]). These rheometers can be used at a constant speed of rotation, or they can be used in an oscillatory mode. These rheometers necessitate the use of shear strains that are 200–1000 times those estimated for cilia. These high shear rates are almost impossible to correlate with in vivo conditions.

In the cone and plate rheometer, the fluid under test is placed between the cone and plate. One of these two platens is rotated which applies a shearing force known as the shear rate. The more viscous the liquid the more stress is set up within it, and is conducted to the upper platens and measured as shear stress. Viscosity is then calculated as the ratio of shear stress to shear rate. Percent strain represents the amplitude of oscillation in units of the spacing between the cone and plate. Thus the lower the percent strain, the lower the oscillation amplitude and the less damage done to the sputum sample.

Magnetic rheometers have been developed using micronsized ferromagnetic particles that can induce small strain, 10–50 times those estimated for cilia. Although there is better in vivo correlation of data with the magnetic rheometer than with the rotational rheometer, the magnetic rheometer is experimentally complex and not suitable for routine testing. Also, mathematical analysis of data from the magnetic rheometer requires the use of a digital computer, which is not suitable for routine clinical use.

Capillary rheometers have been used to measure physiologic fluid viscosity and elasticity for small samples. Viscosity is measured by determining the fluid flow rate in response to a known pressure drop. The recoverable shear strain is determined when this differential pressure is returned to zero. The strains applied to induce fluid flow in capillaries in these instruments are about 10,000 times those estimated to be produced by the cilia and therefore do not correlate with in vivo conditions (Yeates et al., Supra).

Rheologic Properties of Sputum

Mechanical clearance of the airways occurs by way of the mucociliary transport system whose functioning mainly depends on the interaction of two major elements: the cilia which correspond to the motor element of the system and the mucus which is the transport element. Secretions are propelled along the lining membranes of respiratory air passages by the activity of the cilia The mucus is made up of a 2-layer system: the lower non viscid layer, also termed periciliary, and the upper gel viscoelastic layer. Puchelle (*Biorheology* 21: 265–272 [1984]) reports that the mucociliary transport rate will decrease with increased viscosity of the periciliary layer. The increased viscosity and elasticity of respiratory mucus in patients subject to respiratory disease characterized by infectious secretions of the airways makes it difficult for them to clear the secretions from the airways, thus contributing to pulmonary insufficiency, lung infection, and death.

Viscosity, the ability of a material to resist deformation, is the most significant property affecting the flow behavior of a fluid. Viscosity is that property of a fluid or semi-fluid that enables it to develop and maintain an amount of shearing stress dependent upon the velocity of flow and then to offer continued resistance to flow.

Newton's law of viscosity states that this force per unit area is proportional to the velocity gradient between the layers. Thus, $\tau=\mu\gamma$, where $\tau$=shear stress, $\mu$=viscosity, and $\gamma$=shear rate. Fluids that follow this behavior are described as Newtonian fluids.

Non-Newtonian fluids do not obey Newton's law of viscosity, thus the viscosity is dependent on the shear rate. Viscosity decreases with increasing shear. Shear is movement of a layer relative to that of an adjacent layer. Sputum is an example of a non-Newtonian fluid. When a shear stress is applied to sputum, it will behave as a gel and deform roughly in proportion to the stress applied. The shear strain is the ratio of the distance the surface moves compared to the depth of the sputum layer and thus is dimensionless.

Elasticity refers to the ability of sputum to store energy, or resist deformation, when subjected to shear forces. Those fluids that are markedly deformed with very little applied stress but that still return to their original shape are referred to as highly elastic. Sputum samples before rhDNase treatment exhibit greater elasticity than viscosity, although the differences are substantially less after rhDNase treatment. Elasticity is more greatly affected by rhDNase treatment than is viscosity, although both decrease. Elasticity is not dependent on the total DNA concentration. A relationship does exist however between the amount of high molecular weight DNA and the measured elasticity.

The property of viscoelasticity refers to the conjoint properties of viscosity and elasticity exhibited by physiologic fluids including sputum. Lethem et al. (*Eur Respir J.* 3:19–23 [1990]) have demonstrated CF sputum viscoelasticity to increase following exogenous DNA addition and Picot et al., Supra show the viscoelasticity of sputum was found to be independent of total DNA content but increased greatly with the in vitro addition of unhydrolyzed long chain calf thymus DNA.

Percent dry weight of sputum is a measurement of the percentage of solids that exists after drying the sputum sample 2 hours at 160° C. Percent dry weight was calculated as 100 minus the % weight lost after drying.

The term "sputum" as used herein refers to expectorated matter made up of saliva and discharges from the respiratory airways. Sputum is a non-Newtonian highly complex material that has a pronounced gel-like structure. Sputum that is purulent has increased viscoelasticity attributed to both mucus glycoproteins and DNA and is characterized by the fluid products of inflammation for example, leukocytes and the debris of dead cells. There is inherent variability in the rheological properties of purulent sputum.

For collection of sputum for use in the assay of the present invention, Byrne, et al., (*Laboratory Tests: Implications for Nursing Care* 2nd Edition Editors Byrne et al., Publisher Addison-Wesley California [1986]) suggest that the patient collect material, raised by several deep coughs, in a container with a lid. Alternatively, sputum can be collected by using a bronchoscope as described in Kim et al., (*Bull. Europ. Physiopath Resp.* 18: 915–927 [1982]).

Centrifugation

Centrifuges are used to isolate solids from liquids or one liquid from another. Centrifuges are also used to effect the settling of a light phase from a heavy phase or to filter suspended solids by magnifying the force of gravity.

Centrifuges are designed to utilize the principle that an object spinning about a central point at a fixed radial distance is acted upon by a force. Although the velocity of the object is constant, its direction is constantly changing and it is acted upon by a centripetal force toward the center of rotation.

Centrifuges generally consist of a rotor or bowl in which the centrifugal force is enacted upon its components, a system to drive and spin the bowl about its axis, a frame to support the system, and an enclosure to contain the rotor and keep the separated products in a discrete state.

In industrial centrifuges, the centrifugal acceleration is many times the gravitational acceleration. Centrifugal force varies with rotational speed and with radial distance from the center of rotation.

Dose of rhDNase

In the present invention, the minimum in vitro rhDNase concentration showing activity in the compaction assay was 1 µg rhDNase/mL sputum. Using one of the current rhDNase dosage forms, 0.25 mg/mL, and assuming that 0.5 mL of the formulation is actually delivered to the lungs and that the sputum volume over which the concentration of rhDNase is deposited is 100 mL, it can be estimated that the final concentration of rhDNase in vivo is 1.25 µg/mL.

Clinical studies using 1 and 4 mg/mL rhDNase solutions have resulted in increased pulmonary function in CF patients (Aitken et al., Supra and Hubbard et al., Supra). After inhalation of 10 mg of rhDNase, concentrations of rhDNase in sputum collected one hour after inhalation typically ranged from 1–20 µg/mL. This is in agreement with the in vitro data and suggests that the concentration of rhDNase in the formulation is sufficient to have an effect on reducing sputum viscoelasticity. Concentrations of rhDNase above the minimum threshold are preferred in order to allow for variations of sputum characteristics and aerosol deposition.

The use of the term "therapeutic" as used herein refers to those agents effective in the treatment of respiratory disease associated with infected airway secretions and includes but is not limited to antibiotics, DNase, mucolytics, antineutrophil elastase agents, and secretory leucoprotease inhibitor.

Further details of the invention are illustrated in the following non-limiting example.

EXAMPLE 1

Compaction Assay of the Sputum of CF Patients Treated with rhDNase

This example shows that in vitro DNase treatment of purulent sputum from patients subject to respiratory disease characterized by infected airway secretion hydrolyzes the long chain DNA present in the samples thereby reducing the viscosity of the sputum. This example shows that results from the compaction assay of the present invention correlate with rheological measurements obtained from the plate and cone rheometer.

Specimen Characterizations and Test Solutions

Purulent sputum samples obtained from hospitalized, rhDNase-naive Cystic Fibrosis (CF) patients were divided into aliquants for DNA evaluation and rheological analysis. The aliquants for total DNA content and length were frozen until analysis and those for rheological measurements were refrigerated until tested (within 24 hours of collection). Sputum dry weight was determined gravimetrically after drying for 2 hours at 160° C. Percent dry weight was calculated as 100 minus the % weight lost after drying. The gene for DNase I was cloned and expressed at Genentech, Inc. as described in Shak et al. Supra [1990]. The expressed rhDNase was used as a 4 mg/ml solution in 1 mM $CaCl^2$ and 150 mM NaCl at pH 7.4. Control additions, termed "diluent", and dilutions of 4 mg/ml rhDNase used the same salt solution minus rhDNase.

Total DNA Content and Length Assays

Sputum sample DNA content was determined by a modification of the diaminobenzoic acid (DABA) assay developed by Kissane and Robins (*J Biol Chem* 233: 184–188 [1958]) which quantitates total DNA concentration independent of length. Previously frozen sputum aliquants were diluted tenfold with the assay diluent (25 mM HEPES, 1 mg/ml bovine serum albumin, 4 mM $CaCl^2$, 4 mM $MgCl^2$, 0.05% polysorbate 20, and 0.01% thimerasol, at pH 7.5) and incubated at 60° C. for one hour. Diluted specimens (50 μL) were pipeted into microtiter plate wells and 50 μL of a 20% 3,5-diaminobenzoic acid hydrochloride (DABA) solution was added after which the plates were tightly sealed. After one hour of incubation at 60° C. the reaction was stopped by the addition of 50 μL of 5N HCl. A Cytofluor (Millipore Corp.) microtiter plate flurometer (with 390 nm excitation and 530 nm emission filters) was used to read the plates. Salmon testes DNA (Sigma) was used to establish a standard curve. Sputum DNA concentrations from 0.125 to 8 nm/ml were measurable. The coefficient of variation for the assay was determined to be <6%.

The length of the DNA in sputum samples was determined qualitatively by agarose gel electrophoresis as described by Shak et al., Supra. The effect of freezing on sputum DNA length was studied by electrophoresing samples with and without one cycle of freezing at −70° C. Samples were diluted four-fold in a buffer containing 100 mM NaCl, 5 mM EDTA, 0.5% SDS, 100 μg/ml proteinase K (Sigma), 50 mM Tris, pH 8.0, and incubated for three hours at 37° C. with occasional mixing. Samples were then electrophoresed in 0.5% agarose gels and stained with ethidium bromide by standard procedures (Sambrook, et al., Molecular Cloning: A Laboratory Manual, 2nd ed. Cold Spring Harbor Laboratory Press [1989]). A 1 Kb DNA ladder having 12 major bands between 500 bp to 12 Kb (Gibco/BRL 5615SA) was used as the molecular weight standard.

Rheometry

Sputum rheological measurements were made at ambient temperature using the Rheometrics Fluid Rheometer (RFR-7800, Rheometrics Inc. Piscataway, N.J.) with a 0.02 radian, 25 mm radius cone and plate tool. Approximately 0.8 ml sputum was placed on the plate with 25 μL of diluent or rhDNase layered onto the top of the sputum. The cone was lowered onto the sample while the bottom plate was slowly rotated at. 5 rpm to evenly distribute the sample across the gap between the cone and plate. Drying at the sample edge was prevented by pipeting 0.1 poise silicon oil (Dow Chemical) onto the exposed edge of the cone. Rotation of the plate was stopped for five minutes to allow the sample to relax. Each preparation was tested at a deformation rate of 10 radians/sec and the percent strain was varied from 10% to 200% in 10% increments. Percent strain is defined as 100 times the distance of the shearing motion divided by the space between the cone and plate of the viscometer. The second strain value, 20% strain, was used for the comparisons between samples and treatments, being the lowest possible strain for accurate measurement. Instrument start-up frequently compromises the first data point and higher strains can damage network structures (Ferry, J *Viscoelastic Properties of Polymers*. 3rd ed. John Wiley and Sons, Inc. New York pg. 245-[1980]) resulting in artifacts and irreproducible data.

Compaction Assay

Approximately 100 μL of sputum was transferred into a tared Eppendorf microcentrifuge tube with a positive displacement pipet (Gilson Microman®, equipped with a stainless steel shaft and plastic plunger). Either rhDNase or control diluent was added as volume equaling 50% of the exact sputum sample weight. Eppendorf tubes were vigorously vortexed for 15 seconds and then incubated for 15 minutes at ambient temperature. Aliquants of the treated sputum were loaded into Kimax-51, 1.5–1.8×90 mm melting point capillary tubes (Kimble Products) using 50 μL Drummond glass capillary tube (Microcaps). The loaded tubes were centrifuged for 20 minutes at 12,000 rpm in a Biofuge A microcentrifuge (Heraeus Sepatech GmbH) equipped with a horizontal, hematocrit-type rotor head (Heraeus Sepatech) and the supernatant/pellet interface subsequently inspected for resolution. On occasion some samples required up to 20 additional minutes to resolve the supernatant-pellet interface clearly. In these cases, all samples loaded on the rotor were centrifuged for the greater duration. The total height of the material loaded into the capillary tubes and the pellet height were measured in millimeters. The percent pellet was calculated as the height of the pellet divided by the height of the total material loaded, multiplied by 100.

Figure 4:
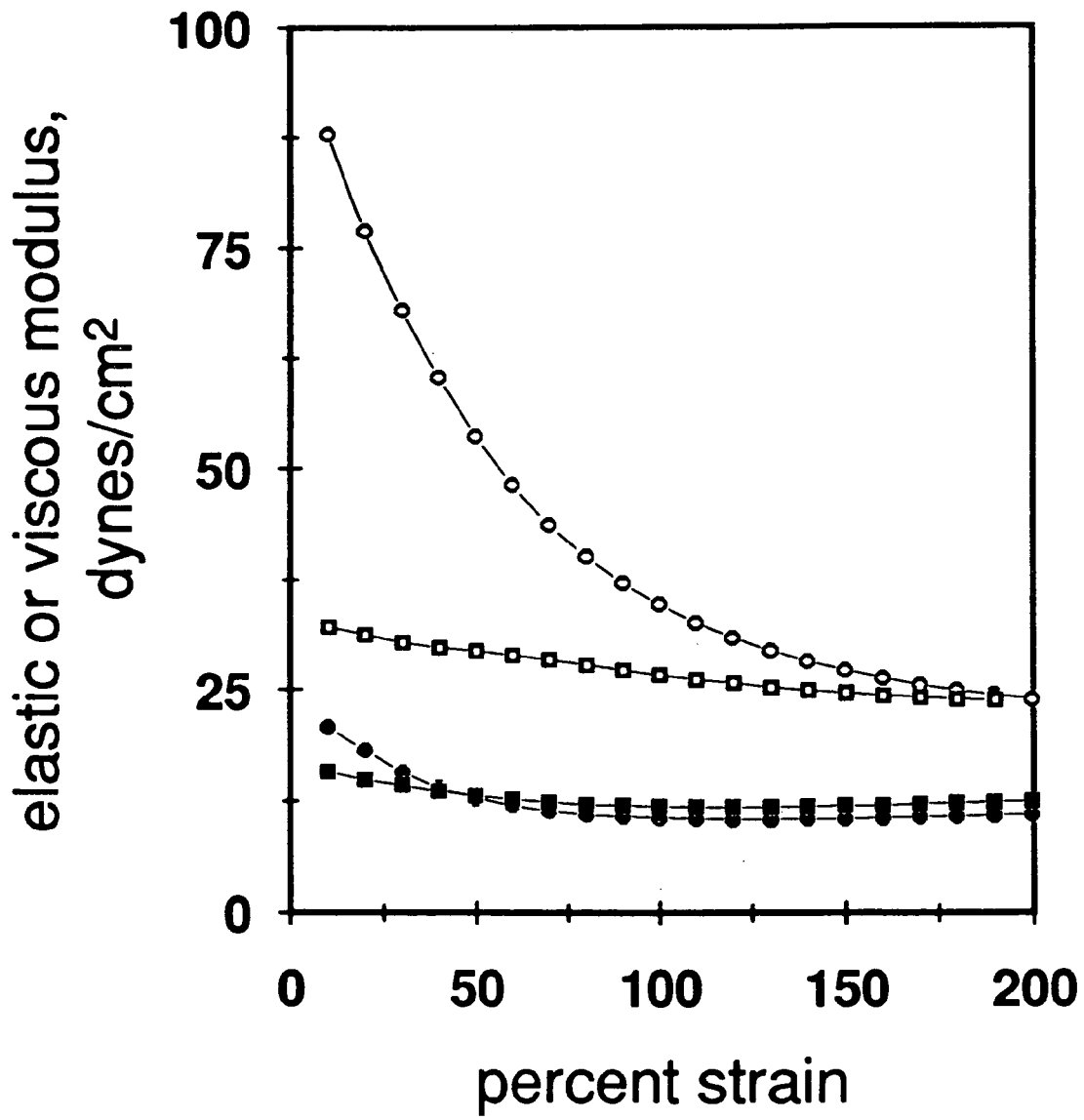
FIG. 4 shows viscosity (squares) and elasticity (circles) moduli measured as a function of percent strain by the dynamic cone and plate viscometer for a representative sputum sample following addition of diluent (open) or rhDNase (filled).

Results:

Viscosity and elasticity moduli measured as a function of strain by the dynamic cone and plate viscometer for a representative sputum sample are shown in FIG. 4. Although treatment with rhDNase reduced measured values of viscosity over the range of strain tested, elasticity was more greatly affected. Using elasticity as the more dramatic rheological criterion for rhDNase effects of CF sputum, several physical properties of six purulent samples were evaluated and presented in FIG. 5. Total DNA concentrations, average percent dry weights, responsiveness to rhDNase treatment assessed by dynamic cone and plate rheometry and the compaction assay showed all six samples to have a considerable DNA content but variable responsiveness to rhDNase treatment. In agreement with previous studies, Rosenbluth et al., Supra, the percent dry weight of the sputum sample does not correlate with either initial elasticity or initial viscosity.

The agarose gel shown in FIG. 2 demonstrates that prior to rhDNase treatment all six samples had variable amounts of very large DNA. Some DNA was too large to enter the gel and was retained at the application site. Smaller fragments of DNA, (varying from approximately 500 base pairs to greater than 12 Kb) could be resolved. All six sputum samples demonstrated complete hydrolysis (less than 500 base pairs) following incubation with 36 mM rhDNase for 20 minutes at 25° C.

Total DNA was detected to a much greater extent in the pellet fraction than in the supernatant of these rhDNase-naive samples following diluent addition and centrifugation in the compaction assay, as demonstrated by FIG. 6. The ratio of DNA distribution between the pellet and supernatant of these rhDNase-naive samples demonstrated a wide range. Samples 4 and 6 had the greatest fraction in the pellet and this correlated with the agarose gel electrophoresis study (FIG. 2) which suggested these same two samples to have the greatest percent of large molecular weight DNA. Sample 3 had the next highest pellet/supernatant DNA ratio (FIG. 6) and qualitatively, the next highest amount of large DNA (FIG. 2). Samples 1, 2, and 5 had the lowest pellet/supernatant DNA ratios and DNA of obviously smaller size.

Following rhDNase treatment, all six samples showed a redistribution of total DNA from the pellet to the supernatant following compaction (FIG. 6). This observation coincides with the agarose gel data (FIG. 2), demonstrating a dramatic reduction in DNA size for each of these samples.

Figure 3:
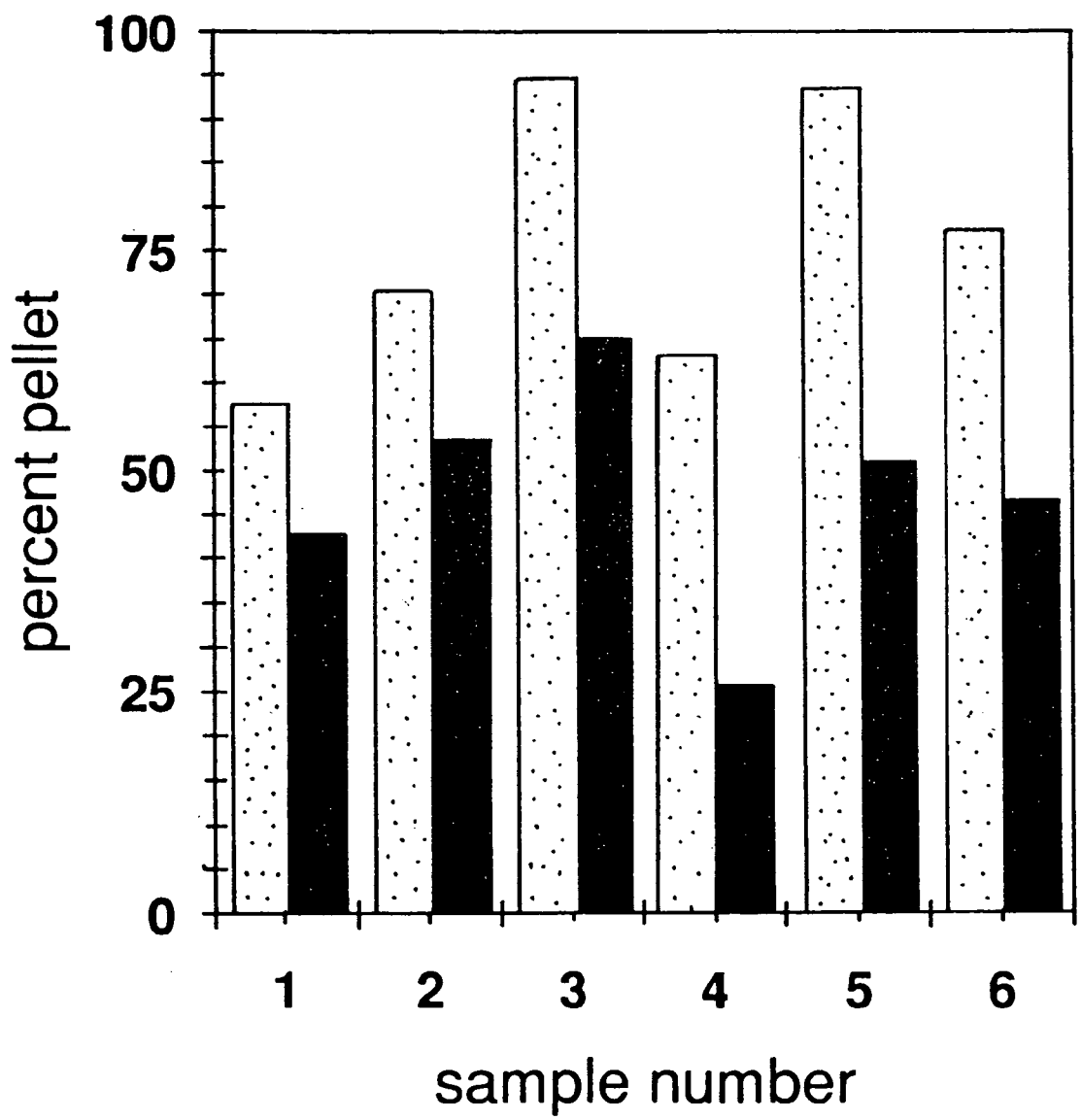
FIG. 3 shows percent pellet heights for the six CF sputum samples obtained in the compaction assay following addition of either diluent, grey bars, or rhDNase, solid black bars.
Figure 7:
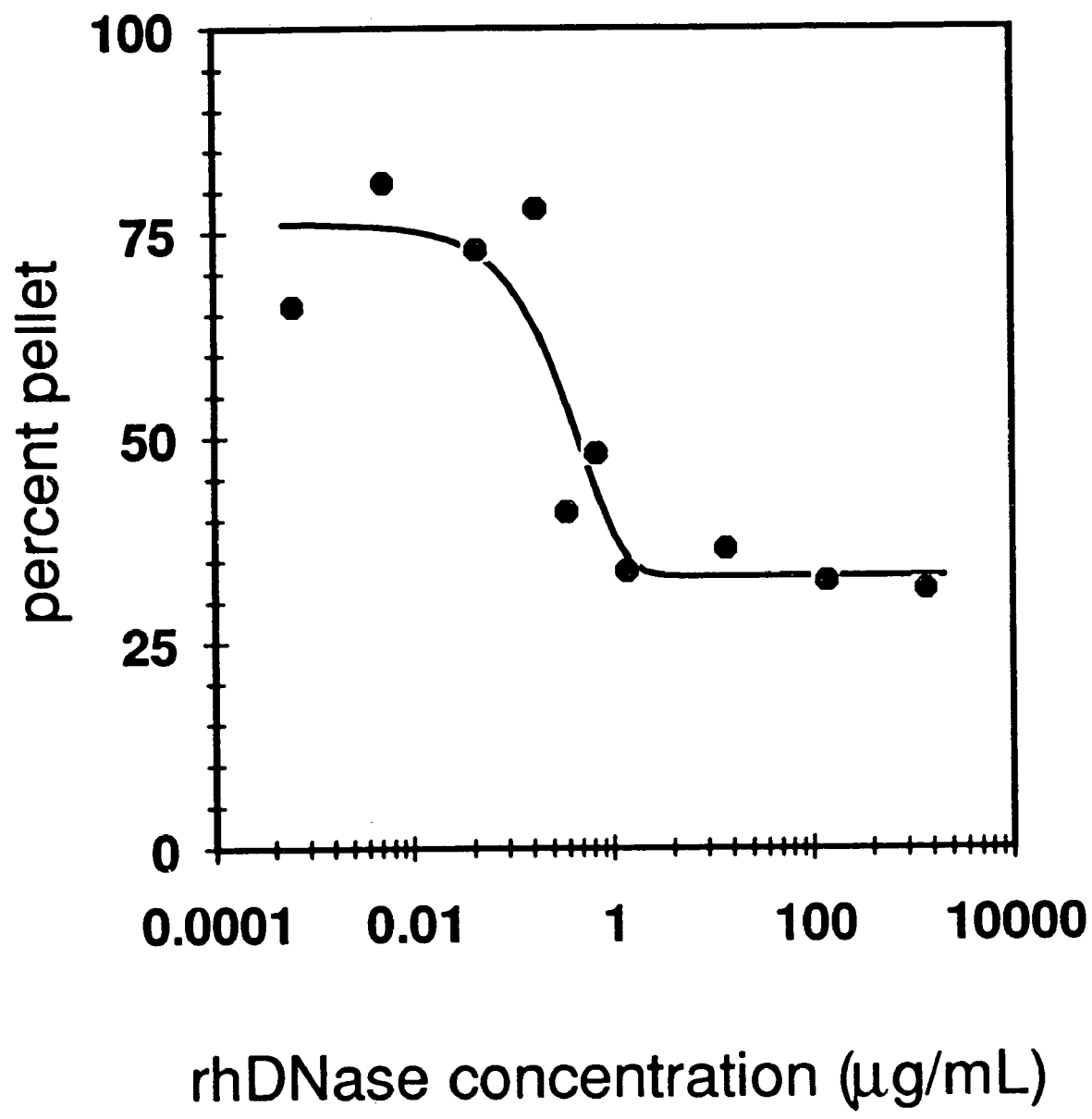
FIG. 7 shows a dose-response curve for rhDNase action of a CF sputum sample. Purulent CF sputum was treated with increasing concentrations of rhDNase and evaluated by the compaction assay. Concentrations of rhDNase were calculated for the volume of sputum plus enzyme addition.
Figure 8:
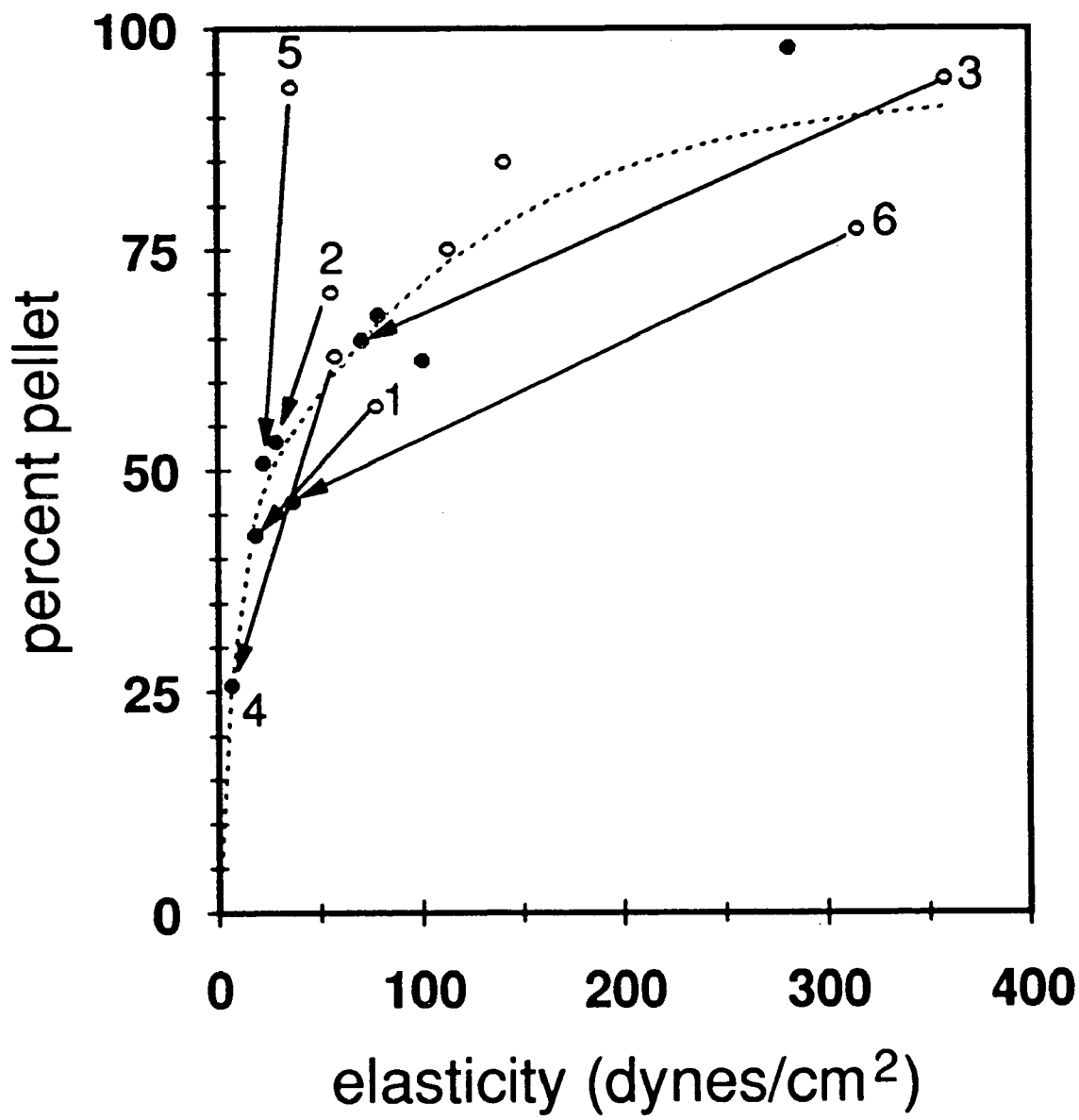
FIG. 8 shows the relationship between compaction assay results and measured elasticity. Elasticity was measured by a dynamic cone and plate viscometer at 20% strain as described. The percent pellet (from compaction assay results) was correlated for the six samples characterized completely in this study as well as four other purulent CF sputum samples. Data points represent both diluent-treated (open symbols) and rhDNase-treated (filled symbols) samples.

The percent pellet heights for the six CF sputum samples obtained in the compaction assay following addition of either diluent of rhDNase are shown in FIG. 3. This data (as well as data from other CF sputum samples) can be correlated to elasticity measurements obtained by the dynamic cone and plate rheometer (FIG. 8). Together these results suggest that the compaction assay is a useful indicator of rhDNase action on purulent CF sputum. The compaction assay was used to obtain a dose-response curve for rhDNase action on a CF sputum sample (FIG. 7). Fitting this data suggests rhDNase to be minimally effective below 0.1 µg/ml and maximally effective above 1 µg/ml in the CF sputum.

The foregoing written description is considered to be sufficient to enable one skilled in the art to practice the invention. Although the foregoing refers to particular preferred embodiments, it will be understood that the present invention is not so limited. It will occur to those ordinarily skilled in the art that various modifications may be made to the disclosed embodiments without diverting from the overall concept of the invention.

All such modifications are intended to be within the scope of the present invention.

All citations cited throughout the specification and the references cited therein, are hereby expressly incorporated by reference.

The invention claimed is:

1. A method for measuring the compaction of a sputum sample from a mammal, comprising obtaining a sputum sample from the mammal, centrifuging said sputum sample until fractionated into supernatant and pellet phases, and measuring the size of the pellet.

2. The method of claim 1 wherein diluent is added to the sputum sample prior to centrifugation.

3. The method of claim 2 wherein the diluent is water added in a volume equaling 50% of the sputum volume.

4. The method of claim 1 wherein said sputum is from a mammal suffering from cystic fibrosis.

5. The method of claim 1 wherein said sputum is from a mammal suffering from pneumonia.

6. The method of claim 1 wherein said sputum is from a mammal suffering from bronchitis.

7. The method of claim 1 wherein said sputum is from a mammal suffering from sinus infections.

8. A method for measuring the effect of a therapeutic on the compaction of a mammalian sputum sample, comprising obtaining a sputum sample from the mammal, adding said therapeutic to the sputum sample, centrifuging said sputum sample until fractionated into supernatant and pellet phases, and measuring the size of the pellet.

9. The method of claim 8 wherein said sputum sample is from a mammal suffering from a respiratory disease associated with infected airway secretions.

10. The method of claim 9 wherein said respiratory disease is cystic fibrosis.

11. The method of claim 9 wherein said respiratory disease is bronchitis.

12. The method of claim 9 wherein said respiratory disease is pneumonia.

13. The method of claim 8 wherein said therapeutic is recombinant human DNase I.

14. The method of claim 8 wherein said therapeutic is an antibiotic.

15. The method of claim 8 wherein the therapeutic is added in a volume equaling 50% of the sputum sample volume.

16. A method of assaying the compaction of a DNase treated sputum sample from a mammal in need of DNase therapy comprising, obtaining a sputum sample from the mammal, adding DNase to the sputum sample, centrifuging the DNase treated sputum sample until fractionated into supernatant and pellet phases, and measuring the size of the pellet.

17. The method of claim 16 wherein said mammal is human and said DNase is recombinant human DNase I.

18. The method of claim 16 wherein said DNase is recombinant human DNase I in a concentration of at least 1 µg rh DNase I/mL sputum.

19. The method of claim 16 wherein said DNase is added in a volume equaling 50% of the sputum volume.

20. A method of determining the relative amount of large molecular weight DNA in a sputum sample, comprising:
    centrifuging said sputum sample until fractionated into supernatant and pellet phases,
    determining the relative size of the pellet phase compared to the size of the supernatant of said sputum sample, and
    comparing the relative pellet size of the sputum sample to the relative pellet size of a reference sputum sample,
    wherein a relative pellet size greater than the reference pellet size indicates greater amount of large molecular weight DNA in the sputum sample and a relative pellet size less than the reference pellet size indicates a lesser amount of large molecular weight DNA in the sputum sample.

21. The method of claim 20 wherein the compaction of said sputum sample is determined by the height of a the pellet relative to the height of the supernatant.

22. The method according to claim 20, wherein the relative size of the pellet phase compared to the size of the supernatant of said sputum sample is determined as the volume of the pellet phase compared to the volume of the supernatant.

* * * * *

UNITED STATES PATENT AND TRADEMARK OFFICE
CERTIFICATE OF CORRECTION

| | | |
|---|---|---|
| PATENT NO. | : 7,193,055 B2 | |
| APPLICATION NO. | : 11/033358 | |
| DATED | : March 20, 2007 | |
| INVENTOR(S) | : Ann L. Daugherty et al. | |

It is certified that error appears in the above-identified patent and that said Letters Patent is hereby corrected as shown below:

Under Column 20, Line 39, please add the following claims as follows:

23. A method of determining the relative amount of large molecular weight DNA in a sputum sample comprising measuring the compaction of the sputum sample and comparing the compaction to the compaction of a reference sputum sample whereby the lesser the compaction of the sputum sample indicates greater amount of large molecular weight DNA.

24. The method of claim 23 wherein the compaction of said sputum sample is determined by centrifuging the sputum sample until fractionated into supernatant and pellet phases and measuring the size of the pellet.

25. The method of claim 24 wherein the compaction of said sputum sample is determined by the height of a the pellet relative to the height of the supernatant.

UNITED STATES PATENT AND TRADEMARK OFFICE
CERTIFICATE OF CORRECTION

PATENT NO. : 7,193,055 B2
APPLICATION NO. : 11/033358
DATED : March 20, 2007
INVENTOR(S) : Ann L. Daugherty et al.

It is certified that error appears in the above-identified patent and that said Letters Patent is hereby corrected as shown below:

Under Column 20, Line 39, please add the following claims as follows: (cont'd)

26. The method of claim 24 wherein the compaction of said sputum sample is determined by the volume of the pellet relative to the volume of the supernatant.

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

PATENT NO.       : 7,193,055 B2
APPLICATION NO.  : 11/033358
DATED            : March 20, 2007
INVENTOR(S)      : Ann L. Daugherty et al.

It is certified that error appears in the above-identified patent and that said Letters Patent is hereby corrected as shown below:

Under Column 20, please add the following claims as follows:
Col. 20, Line 39

23. A method of determining the relative amount of large molecular weight DNA in a sputum sample comprising measuring the compaction of the sputum sample and comparing the compaction to the compaction of a reference sputum sample whereby the lesser the compaction of the sputum sample indicates greater amount of large molecular weight DNA.

24. The method of claim 23 wherein the compaction of said sputum sample is determined by centrifuging the sputum sample until fractionated into supernatant and pellet phases and measuring the size of the pellet.

25. The method of claim 24 wherein the compaction of said sputum sample is determined by the height of a the pellet relative to the height of the supernatant.

UNITED STATES PATENT AND TRADEMARK OFFICE
CERTIFICATE OF CORRECTION

PATENT NO. : 7,193,055 B2
APPLICATION NO. : 11/033358
DATED : March 20, 2007
INVENTOR(S) : Ann L. Daugherty et al.

It is certified that error appears in the above-identified patent and that said Letters Patent is hereby corrected as shown below:

Under Column 20, please add the following claims as follows (cont'd):

26. The method of claim 24 wherein the compaction of said sputum sample is determined by the volume of the pellet relative to the volume of the supernatant.

Signed and Sealed this

Twenty-first Day of August, 2007

JON W. DUDAS
*Director of the United States Patent and Trademark Office*